United States Patent [19]
O'Neil

[11] Patent Number: 5,318,539
[45] Date of Patent: Jun. 7, 1994

[54] LIQUID FEEDING APPARATUS UTILIZING CAPILLARY TUBING, AND SYRINGE DRIVER

[75] Inventor: Alexander G. B. O'Neil, 102 Lawler Street, Subiaco 6008, Perth, Australia

[73] Assignees: Alexander G. B. O'Neil; Christine O'Neil, both of Perth, Australia

[21] Appl. No.: 778,500

[22] Filed: Oct. 17, 1991

Related U.S. Application Data

[63] Continuation-in-part of Ser. No. 346,980, Jun. 16, 1989, abandoned.

[30] Foreign Application Priority Data

Oct. 17, 1986 [GB] United Kingdom ............. PI8624949
Jul. 20, 1987 [AU] Australia ..................... 3234

[51] Int. Cl.$^5$ .......................... A61M 1/00; A61M 5/20
[52] U.S. Cl. ..................... 604/118; 604/121; 604/151; 604/248; 604/135
[58] Field of Search .............. 604/134–139, 604/152, 246–248, 257, 118, 121; 128/DIG. 12, DIG. 13

[56] References Cited

U.S. PATENT DOCUMENTS

| | | | |
|---|---|---|---|
| 1,633,293 | 6/1927 | Smiley | 604/135 |
| 3,451,393 | 6/1969 | Sarnoff | 604/135 |
| 3,877,428 | 4/1975 | Seagle et al. | 604/248 |
| 3,888,239 | 6/1975 | Rubinstein | 604/135 |
| 4,034,754 | 7/1977 | Virag | 128/214 R |
| 4,381,006 | 4/1983 | Genese | 604/135 |
| 4,597,754 | 7/1986 | Thill et al. | 604/135 |
| 4,626,243 | 12/1986 | Singh et al. | |
| 4,743,235 | 5/1988 | Waldbillig et al. | 604/250 |
| 4,909,783 | 3/1990 | Morrison | 604/30 |

FOREIGN PATENT DOCUMENTS 0583521 10/1958 Italy ............................ 604/135

OTHER PUBLICATIONS

Mahood et al., *Use of Capillary Tubing for Flow Measurement*, Instruments & Automation, vol. 27, pp. 460–461, Mar. 1954.

*Primary Examiner*—John D. Yasko
*Assistant Examiner*—Adam J. Cermak
*Attorney, Agent, or Firm*—Ratner & Prestia

[57] ABSTRACT

A method of manufacturing flexible thick-wall capillary tubing, comprising the steps of extruding a plastics sheath around a filament of uniform diameter, and withdrawing the filament from the sheath to form a length of tubing having a capillary bore which has been defined by the filament. The method enables the manufacture of fine-bore capillary tubing having a tightly controlled bore diameter.

The invention also provides a method of low flow rate metering of a liquid by utilising a length of such tubing as a flow restriction, and apparatus for carrying out the method. This method and apparatus are particularly suited to controlling very low rates of flow of drugs or other injectable liquids to a patient over a prolonged period, in an arrangement which can readily be carried on the patient's arm to alow the patient mobility while being injected.

The invention further provides a syringe driver for use with the drug-feeding method and apparatus, the syringe driver including a spring selected according to a novel formula to deliver a syringe-driving force that varies by less than a predetermined limit.

12 Claims, 10 Drawing Sheets

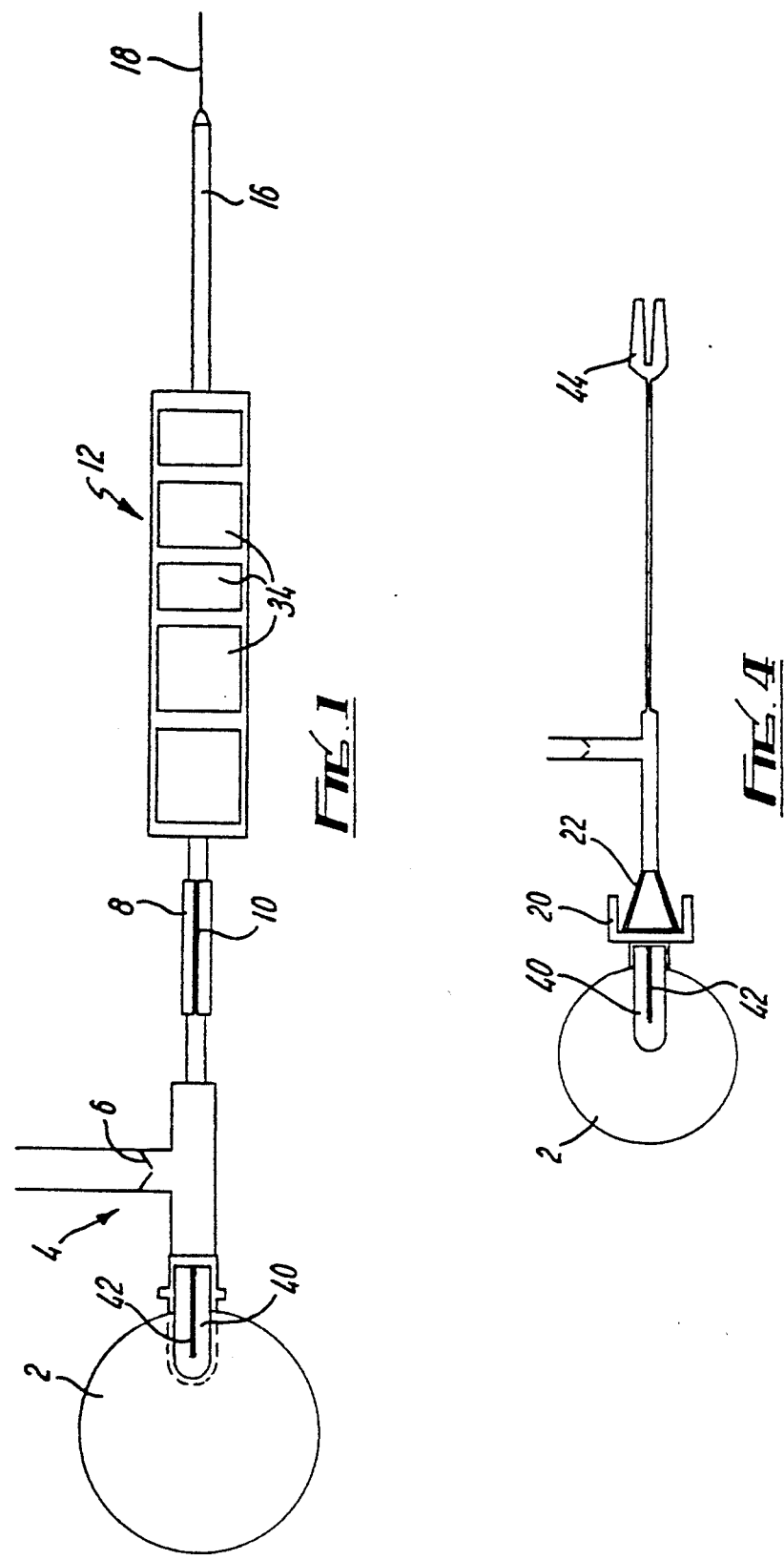

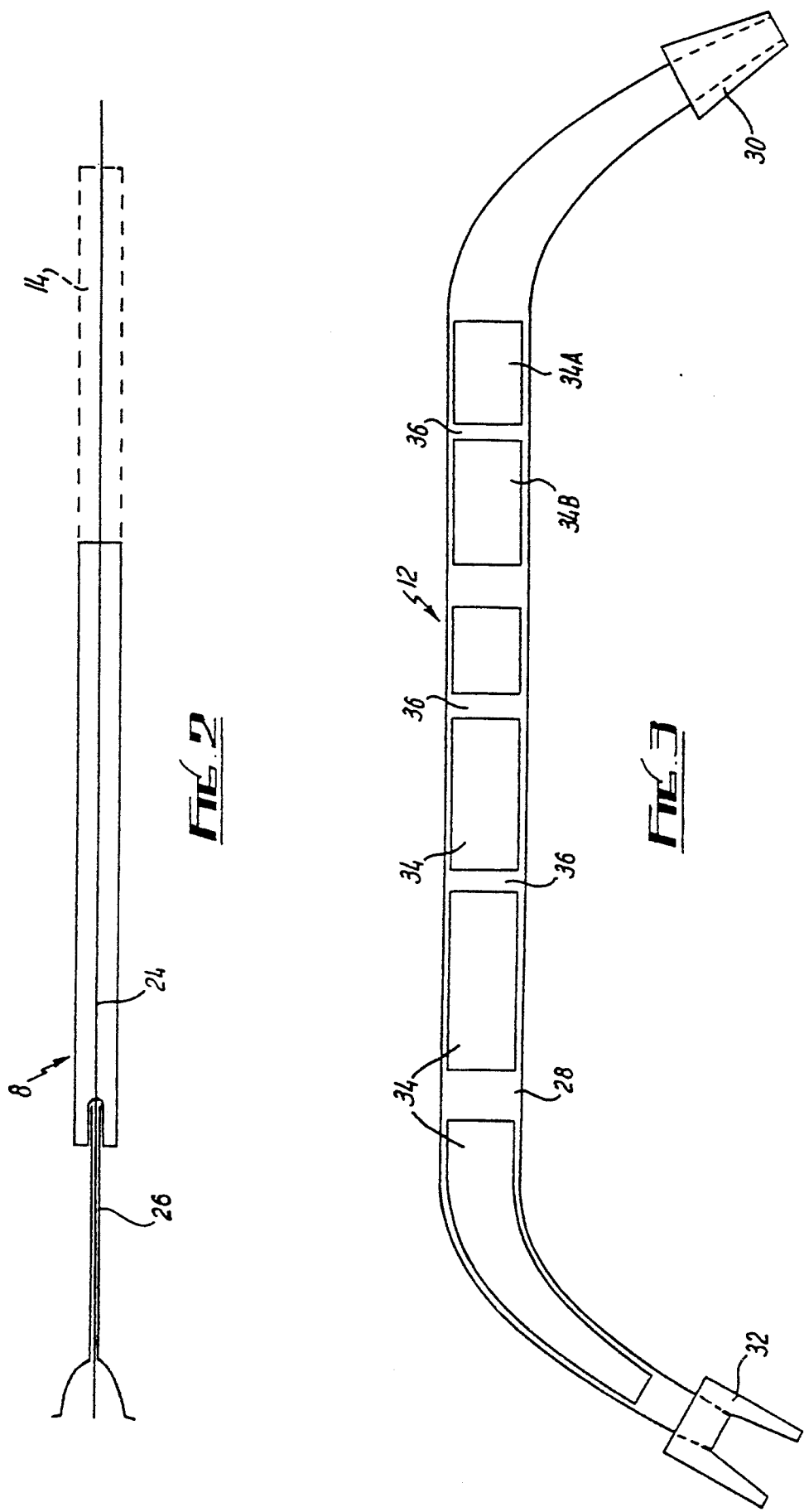

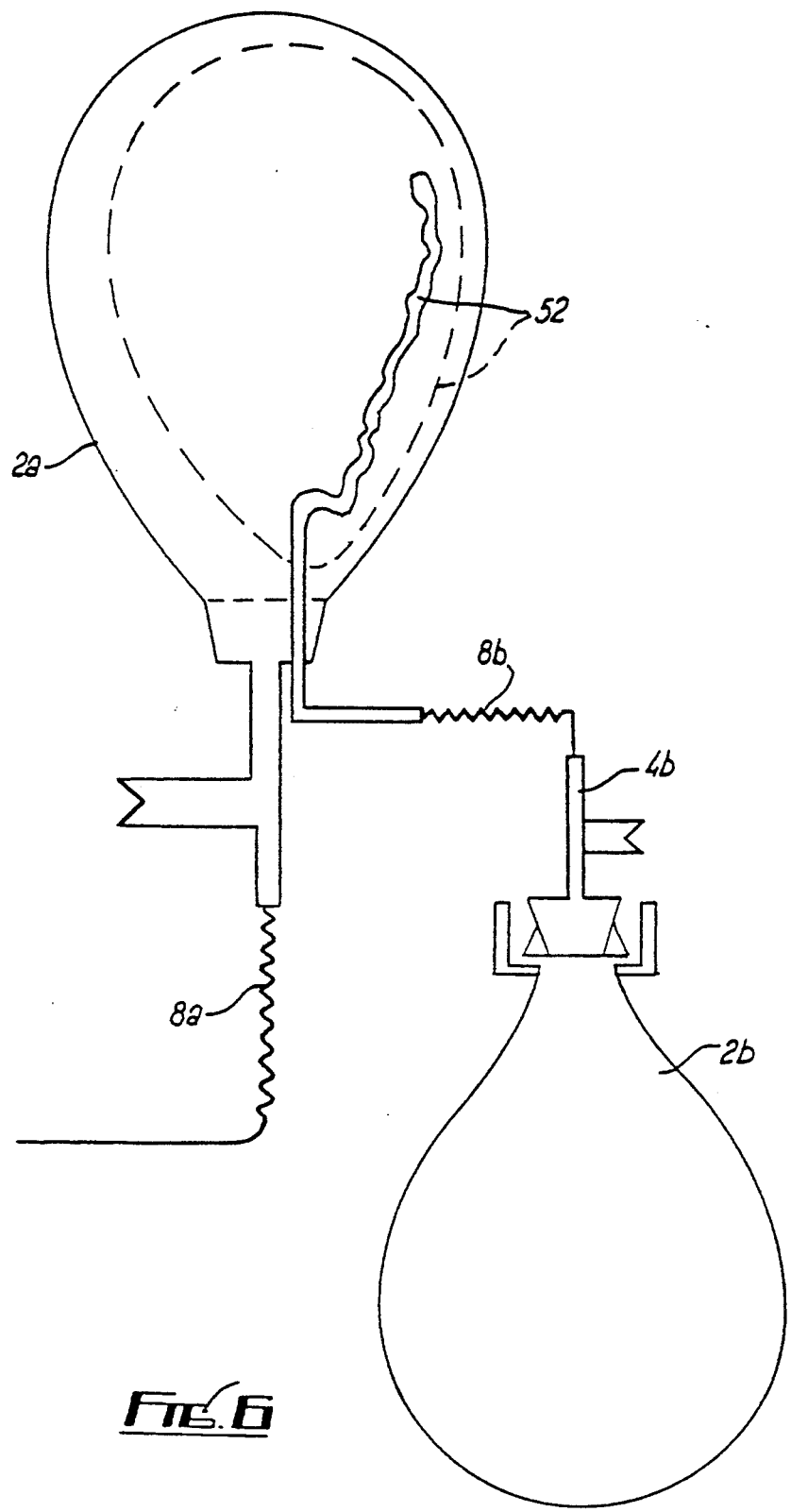

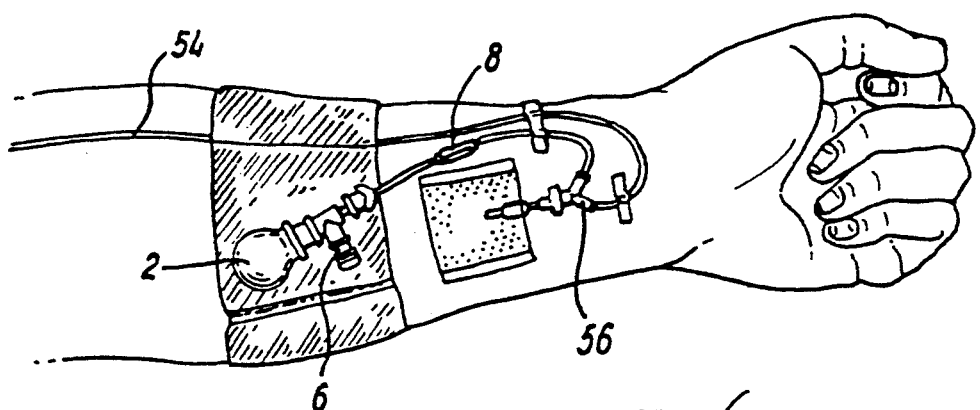
FIG. 7
FIG. 8
FIG. 9
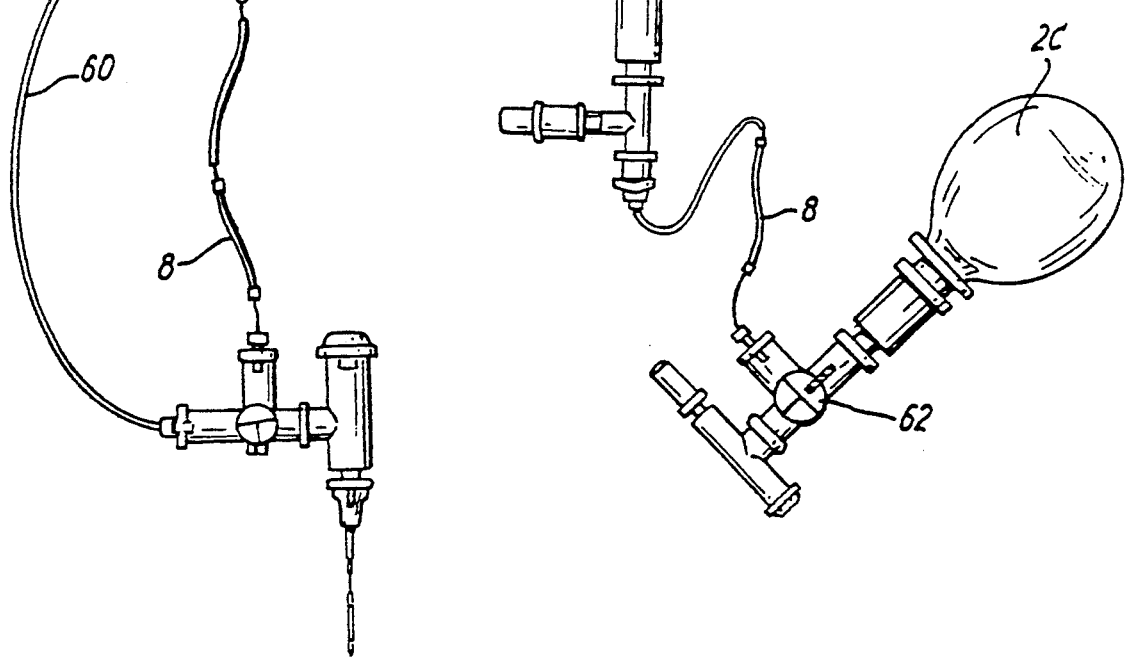

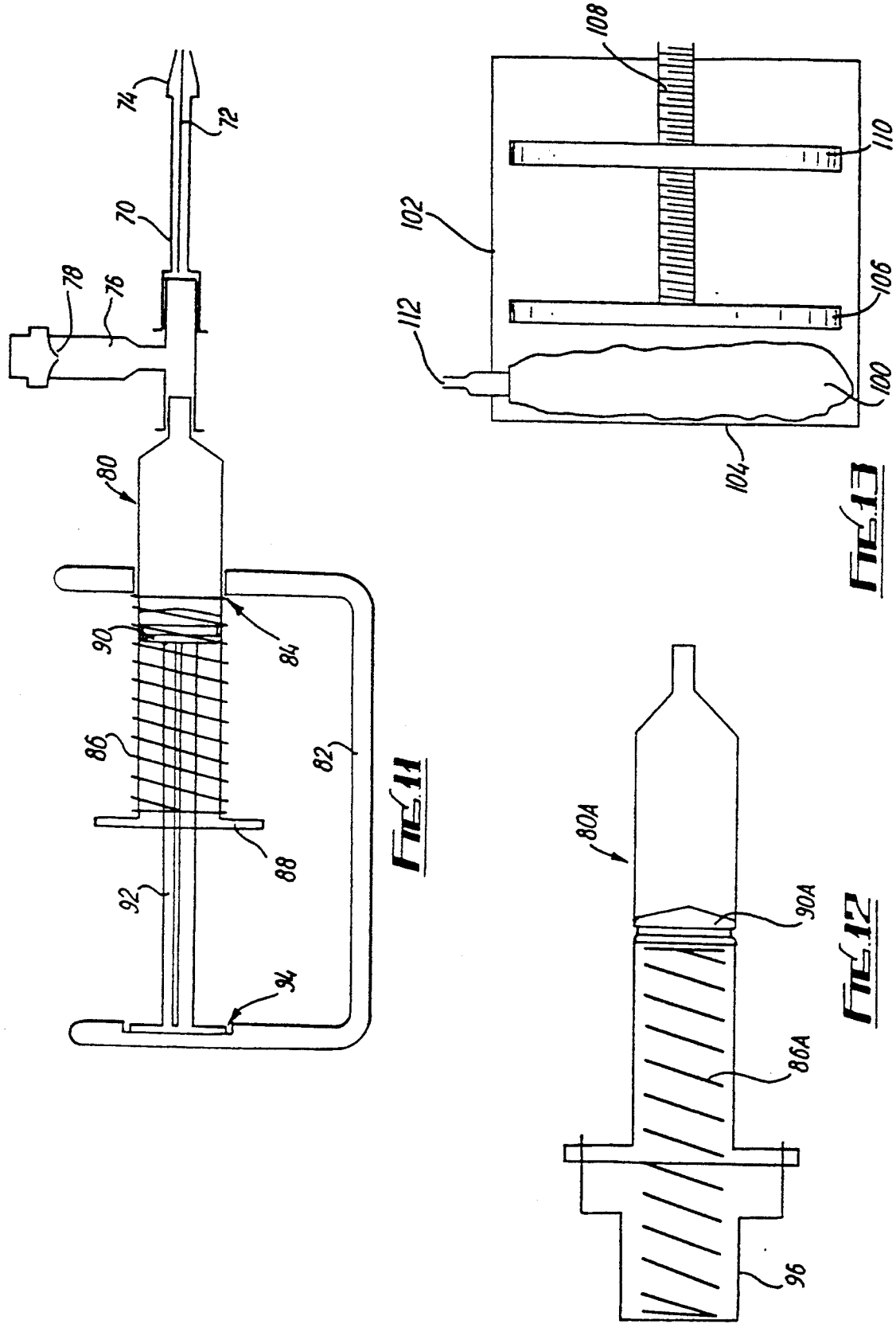

LIQUID FEEDING APPARATUS UTILIZING CAPILLARY TUBING, AND SYRINGE DRIVER

This application is a Continuation-in-Part of Application Ser. No. 07/346,980 filed Jun. 16, 1989, now abandoned.

This invention relates to a method of manufacturing flexible thick-wall capillary tubing, a method of feeding drugs or other liquids in a controlled manner using such tubing, and to apparatus including such tubing, for use in carrying out the drug-feeding method.

It is often necessary to provide a constant or intermittent flow of injected liquid drugs to a patient under treatment, as for example in the case of a diabetic, and hitherto such controlled feeding of drugs has been carried out by using syringe-driver apparatus such as electrically-driven screw mechanisms actuated in a programmed manner by microprocessor. These apparatus, however, are expensive and require power sources that render the apparatus bulky and unwieldy.

Other systems that have previously bee proposed employ resilient drug reservoirs which contain drugs under pressure, causing inflation of the reservoir to produce a positive head of liquid. This pressure head results in the drug being driven from the reservoir along a narrow-bore tube to the patient. Such systems are described for example in U.S. Pat. Nos. 3,469,578 (Bierman) and No. 3,486,539 (Jacuzzi). In the Bierman and Jacuzzi Patents the outflow rate of liquid drug from the reservoir is controlled by a porous plug through which the drug is led, the porosity of the plug determining the rate of drug flow.

Other similar arrangements have been proposed such as in U.S. Pat. No. 3,468,308 (Bierman) in which the flow rate from the reservoir is controlled either by passage through a rigid needle or through a porous mass, and UK Pat. No 1,454,310 (Alza Corporation) in which the flow is controlled by an adjustable valve or variable restriction in the outlet line from the reservoir.

U.S. Pat. No 4,626,243 (Singh et al) provides a reservoir that deforms under applied external pressure from a pressurised gas cylinder, and the outflow of liquid from the reservoir is determined by a flow restrictor in the outlet line comprising a narrow-bore tube. The bore can be provided by a length of hypodermic needle tubing or by a short length of thick-walled elastomer tube contained within an outer metallic tube.

In all of these prior art arrangements the apparatus for controlling the outflow of liquid from the reservoir is disposed in a rigid section of liquid line between the reservoir and a discharge line which is usually in the form of flexible tubing.

It is often necessary or desirable to provide an extremely slow rate of delivery of a drug to a patient, perhaps of the order of 0.1 millilitre per hour, but the prior art apparatus has been able to provide flow rates only down to about 2 milliliters per hour. This is due to the limitations dictated by the nature of the above flow restricting devices, all of which are rigid structures inserted in the flow line; as the resistance to flow increases with increasing length of the flow restrictor, the overall flexibility of the tubing between the reservoir and the patient suffers if very slow rates of delivery are required.

It is therefore a primary object of the invention to provide a method of manufacturing flexible thick-wall capillary tubing suitable for use as a liquid flow restriction in apparatus such as, for example, a drug-feeding apparatus for very low-rate delivery of drugs to a patient, such tubing being manufactured to have a capillary bore of about 250 microns or less, and tightly controlled bore dimensional tolerances.

It is a further object of the invention to provide a method of restricting the delivery of a liquid from a pressurisable liquid source along a liquid conduit to a liquid recipient by constituting at least part of the liquid conduit as a liquid flow restriction in the form of a length of flexible thick-wall capillary tubing, and it is another object of the invention to provide apparatus for carrying out this invention. Inasmuch as the pressurisable liquid source in such apparatus may comprise a syringe, it is desirable that the syringe.. plunger be driven, preferably over prolonged periods, by a syringe driver delivering a driving force to the plunger that is nearly constant during the delivery period and varies over the extent of plunger travel by less than a predetermined limit, e.g. ±10 per cent; accordingly, it is a still further object of the invention to provide such a syringe-driver apparatus, preferably in a form which is easily and reliably coupled to the driven syringe without the need for tools.

According to a first aspect of the present invention, there is provided a method of manufacturing a length of flexible thick-wall capillary tubing, said method comprising the steps of:

(a) providing a filament having a substantially uniform external diameter along a length of said filament at least equal to the intended length of tubing to be manufactured;

(b) forming a plastics sheath around said filament along at least said length of filament, said sheath having an internal diameter substantially defined by said external diameter of said filament, said sheath having an external diameter at least twice said internal diameter of said sheath; and (c) longitudinally withdrawing said filament from said sheath to form said length of tubing wherein the capillary bore thereof has been defined by said filament.

The external diameter of said filament is preferably in the range from about 25 microns to about 250 microns, and more preferably in the range from about 75 microns to about 200 microns.

The external diameter of said sheath is preferably at least five times and more preferably at least fifty times the internal diameter of said sheath.

The length of said substantially uniform-diameter length of said filament is preferably in the range from about 1 centimeter to about 40 centimeters.

Said filament may be a metal wire, for example a stainless steel wire, or said filament may comprise at least one carbon fibre.

Said plastics sheath is preferably formed around said filament by the step of extruding a plastics material around said filament. The material of said sheath is preferably at least one material selected from the group consisting of polyvinyl chloride, polyurethane, and silicone elastomer.

Said filament is preferably longitudinally withdrawn from said sheath by the steps of:

(a) anchoring one end of said filament; and (b) repeatedly propagating a strain wave along said sheath from the end thereof adjacent said one end of said filament towards the opposite end of said sheath while applying longitudinal traction to said sheath in the direction of propagation of said strain wave to progressively detach said sheath from said filament, until said sheath is completely separated from said filament. Said strain wave is preferably induced by the step of applying a localised compressive force to said sheath and said strain wave is preferably propagated by the step of progressively displacing the locality of the application of said localised compressive force in said direction of propagation.

According to a second aspect of the present invention there is provided a method of restricting the delivery of a liquid from a pressurisable liquid source along a liquid conduit to a liquid recipient to a liquid delivery rate of less than 1 millilitre per hour, said method comprising the step of constituting at least part of said liquid conduit as a liquid flow restriction in the form of a substantially predetermined length of flexible thick-wall capillary tubing having a ratio of the external diameter thereof to the bore diameter thereof in excess of 2:1, a bore diameter of less than about 250 microns, and a length of less than about 40 centimeters.

According to a third aspect of the present invention there is provided a liquid-feeding apparatus for feeding a liquid to a recipient at a rate of less than 1 millilitre per hour, said apparatus comprising:
(a) a pressurisable source of the liquid;
(b) said source having a liquid outlet;
(c) a transfer fitting for transfer of the liquid to the recipient;
(d) a liquid conduit coupling said liquid outlet of said source to said transfer fitting for conveying the liquid from said source to said transfer fitting;
(e) said liquid conduit comprising a liquid flow restriction;
(f) said liquid flow restriction comprising a length of flexible thick-wall capillary tubing;
(g) said tubing having a ratio of the external diameter thereof to the bore diameter thereof in excess of 2:1;
(1) said tubing having a bore diameter of less than about 250 microns; and
(i) said tubing having a length of less than about 40 centimeters.

Said tubing preferably has a bore diameter in the range from about 25 microns up to about 250 microns, and more preferably in the range from about 75 microns up to about 200 microns.

Said tubing preferably has the ratio of the external diameter thereof to the bore diameter thereof in excess of 5:1, and more preferably in excess of 50:1.

Said tubing preferably has a length in the range from about 1 centimeter up to about 40 centimeters, and more preferably a length of about 8 centimeters.

Said tubing is preferably composed of at least one material in the group consisting of polyvinyl chloride, polyurethane, and silicone elastomer.

Said pressurisable source preferably comprises a container having a variable internal volume and pressurisation means stressing said container to tend to reduce the internal volume thereof.

Said container and said pressurisation means may be conjoined as an elastically expandable bladder which may contain an insert having a volume greater than the internal volume of said bladder in the unexpanded state thereof.

Alternatively, said container may comprise a syringe having a body with a bore therein and a plunger slidingly sealed to said bore to define said variable internal volume, and said pressurisation means may comprise a housing and an elastically compressible spring therein, said housing having a coupling by which said housing is connectible to said body of said syringe, said spring being disposed within said housing to have one end of said spring act on said plunger of said syringe when said housing is connected to said body of said syringe to have the other end of said spring react against said housing, said spring being dimensioned and precompressed to act on said plunger with a force that varies over the full travel of said plunger by less than a predetermined limit.

Said body of said syringe may comprise an opposed pair of projections functioning as finger grips in manual operation of said syringe, and said coupling is preferably a bayonet coupling dimensioned to connect to said projections and to be connectible thereto by sequential relative longitudinal movement and relative rotational movement through a limited angular extent.

Said spring is preferably a helically-coiled compression spring having a free length equal to A, a yield-point length equal to S, and a housing-defined maximum length within the housing equal to L, the spring and the housing being so dimensioned that A is greater than or equal to $3L-2S$, and more preferably so dimensioned that A is greater than or equal to $5L-4S$. The yield-point length S is the length of the spring when the yield point is reached, the yield point being a condition of the spring at which the metal of the spring is at the elastic modulus or limit. The yield-point length is usually close to the fully-compressed coil-bound length of the spring.

According to a fourth aspect of the present invention there is provided syringe-driver apparatus for driving a syringe comprising a syringe body having a bore therein and a liquid outlet at one end of said bore, said syringe further comprising a syringe plunger slidingly sealed to said bore to define a variable volume within said bore between said plunger and said liquid outlet, said volume being varied by travel of said plunger along said bore, said syringe-driver apparatus comprising a housing and an elastically compressible spring therein, said housing having a coupling by which said housing is connectible to said syringe body, said spring being disposed within said housing to have one end of said spring act on said syringe plunger when said housing is connected to said syringe body and to have the other end of said spring react against said housing, said spring being dimensioned and precompressed to act on said syringe plunger with a force that varies over the full travel of said syringe plunger by less than a predetermined limit.

Said syringe body preferably comprises an opposed pair of projections functioning as finger grips in manual operation of said syringe, and said coupling is preferably a bayonet coupling dimensioned to connect to said projections and to be connectible thereto by sequential relative longitudinal movement and relative rotational movement through a limited angular extent.

Said spring is preferably a helically-coiled compression spring having a free length equal to A, a yield-point length equal to S, and a housing-defined maximum length within said housing equal to L, said spring and said housing being so dimensioned that A is greater than or equal to $3L-2S$, and more preferably so dimensioned that A is greater than $5L-4S$.

The bore diameter of the capillary tubing can be selected depending on the desired liquid flow characteristics, and in general it has been found that for drug infusion a bore diameter of from 50 microns to 250 microns (0.05 mm to 0.25 mm) can provide readily controllable and precise flow. As the resistance to flow depends on the length as well as the diameter of the bore, a number of tubes may be interconnected to provide a long flow path for the fluid if greater resistance, and therefore slower flow, is required.

The flexible nature of the tube allows such length extensions to be made without rendering the apparatus unwieldy or obtrusive.

The reservoir may be in the form of a cylinder, such for example as a syringe barrel having a piston or plunger therein for moving liquid in the cylinder to an outlet at one end of the cylinder; the piston and cylinder may be relatively movable under the action of a spring which may be disposed internally or externally of the cylinder.

Alternatively, the reservoir may be in the form of an expandable resilient bladder member which can be inflated with liquid to pressurise it, the pressure then being relieved by outflow of the liquid through the flexible tube. In order to avoid the problem of substantial loss of pressure as the bladder nears empty, which would leave a quantity of liquid in the bladder with insufficient pressure to force it through the tube, it is of advantage to occupy such "dead space" with an insert of greater volume than the unexpanded volume of the bladder. The reservoir wall then retains a degree of resilience, so that there is always a positive pressure exerted on liquid within the reservoir. The insert should have liquid channel means to allow escape of liquid from the collapsing reservoir. The insert may have a shape which stretches the collapsing reservoir in a manner which minimises the pressure drop between the reservoir when full and the reservoir when collapsed; such an insert is preferably of elongate, narrow profile.

A further method of reducing pressure loss in the bladder is to provide a second resilient inflatable reservoir of greater volume than the bladder in communication with the bladder so that the reservoir provides liquid which replenishes the bladder as the bladder discharges liquid through the flexible tube.

The bladder may be formed by injection moulding.

The invention also provides a method of feeding liquids, comprising loading a series of liquids in a predetermined order and quantity into a container, applying pressure to an inlet of the container and allowing the liquids to emerge from an outlet of the container in said predetermined order and quantity under the influence of said pressure.

The container is preferably in the form of a conduit into which are loaded the liquids to be fed. The liquids may be predetermined quantities and types of drugs for injection into a patient, the drugs being separated in the conduit by gas such as air, or by further liquids immiscible with the drugs.

The apparatus of the invention may be provided in a branch line of liquid conduit. This allows a predetermined quantity of a drug, for example, to be injected at a controlled rate into a liquid conduit to a patient without interrupting flow through the liquid conduit. A valve may be provided in branch line for connection and disconnection of the reservoir as required, and the valve may be either upstream or downstream of the flexible tube.

The apparatus of the invention may be adapted to provide a portable system for providing a supply of drugs to a patient, by providing an injection needle at the downstream end of the apparatus and connection means for mounting the apparatus on a limb or other part of the body of the patient.

The apparatus and method of the invention may also provide a switching system or detonator for industrial application, by loading into the liquid reservoir an activating liquid preceded by a non-activating liquid, so that emergence of the activating liquid provides the switch or detonation at a predetermined time for initial actuation of the apparatus.

It will be appreciated that the apparatus of the invention can be gravity-independent in operation, and therefore adaptable to portable use and to use in weightless conditions such as in outer space. The portable aspect of the apparatus allows it to be used for emergency rapid-liquid-replacement conditions. Preferably a pressure head equivalent to 200–600 mm of mercury is derived from the reservoir.

Embodiments of the present invention will now be described with reference to the accompanying drawings, in which:

FIG. 1 is a side view of apparatus of this invention;

FIG. 2 is a side view illustrating a method of manufacture of the invention;

FIG. 3 is a side view of the drug storage reservoir shown in FIG. 1;

FIG. 4 is a sectional side view showing the fitting of the balloon of FIG. 1 onto the T-piece;

FIG. 6 is a schematic side view of apparatus of the invention for maintaining a constant liquid pressure within a supply balloon;

FIG. 7 is a side view of portable apparatus of the invention;

FIGS. 8 and 9 are views of alternative forms of the apparatus of the invention incorporating flushing systems;

FIG. 11 is a sectional side elevation of a further embodiment of the apparatus of this invention;

FIG. 12 is a sectional side elevation of an alternative form of syringe to that shown in FIG. 11;

FIG. 13 is a schematic view of an alternative form of reservoir and ejection means for fluid;

Figure 5:
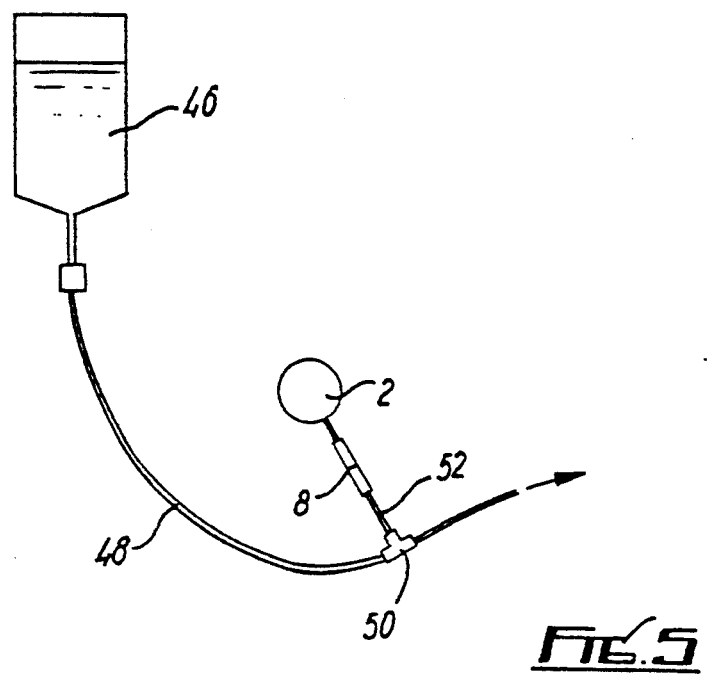
FIG. 5 is a side view of apparatus of the invention for continuous saline supply with intermittent drug supply.

Referring first to FIG. 1, the apparatus of this embodiment of the invention comprises a moulded silicone rubber bladder or balloon 2, a T-piece adaptor 4 having a one-way valve 6 connected to the leg of the T, a flow-resistance conduit 8 of silicone rubber capillary tubing having a central bore 10 through it, a drug container 12 containing discrete sections or doses 34 of drugs in a predetermined order and quantity for feeding to a particular patient, tubing 16 connected to the outlet of the container 12 and a needle 18 for insertion in the patient. The balloon 2 is relatively thick-walled at 0.4 mm and is thereby capable of withstanding high pressure within it. The balloon is manufactured by a liquid silicone moulding technique onto a collar 20 (FIG. 4) which is 8 mm in length and is held in place on the T-piece 4 by a reverse-tapered surface 22 producing a tight fit.

A plastics insert 40 extends into the balloon 2 to limit the extent of collapse of the balloon walls on emptying. The insert 40 is selected to ensure that the collapsed balloon (shown dotted in FIG. 1) retains an element of resilience, so that a positive pressure is always maintained for liquid within the balloon 2. The insert 40 has longitudinal grooves 42 in its outer face to allow outflow of liquid along them as the balloon 2 deflates. This assists in maintaining a constant pressure of liquid from the balloon during its deflation and ensures that the balloon 2 empties itself of liquid on deflation.

The flow-resistance conduit 8 is formed (FIG. 2) by extruding silicone rubber as a 4 mm diameter solid cylinder around a monofilamentary wire 24 of a diameter in the range from 0.025 to 0.076 millimeters, in the present case 0.063 mm diameter and then stripping sections 14 of the extrusion from the wire 24 to provide narrow-bore conduits of a required length of 8 cm. A needle 26 is passed around the wire 24 into the silicone rubber body, so that the wire 24 acts as a guide for the needle 26 to pass centrally through the body; without the wire the tight-fitting needle 26 tends to move off-centre as it passes along the body. After insertion of the needle 26 the wire 24 is removed. The wire 24 may be a stainless steel wire. As an alternative to the use of a metal wire as the capillary-bore-defining filament, one or more carbon filaments may be employed.

As an alternative to the use of a silicone elastomer, the material of the sheath extruded around the wire or other bore-defining filament may be polyvinyl chloride, or a polyurethane, or a mixture of two or more of these materials.

The drug container 12 is in the form of a thin tube 28 (FIG. 3) having flexible tubing terminating at its respective ends in a male luer lock fitting 30 and a female luer lock fitting 32. A series of drug doses 34 are inserted sequentially within the tube 28 as shown in FIGS. 1 and 3, each dose 34 being separated from adjacent doses by an air gap 36, although in other embodiments the air 36 can be replaced by a liquid such as an oil which is immiscible with the drugs.

The drug doses 34 are selected to be appropriate to the needs of a particular patient over a period of time, and are packaged within the tube 28 so as to travel along it without mixing with adjacent doses. The concentrations and quantities of the doses are also selected to compensate for the gradual reduction in pressure of the balloon 2 as it empties.

In use, the balloon 2 is inflated to a pressure of 300 mm of mercury by introduction of water through the one-way valve 6, so that the balloon 2 acts as a supply of high-pressure liquid to the resistance conduit 8 through the T-piece adaptor 4.

The small bore of the conduit 8 ensures slow leakage of water through it at a rate of 1 millilitre per hour, under the driving pressure provided by the water-inflated balloon 2. This pressurised water enters the drug container 12 from the balloon 2 and pushes the drug doses 34 slowly towards the outlet of the container 12 and sequentially along the outlet tubing into the needle 18 which is inserted into the patient. Each dose 34 is thereby delivered to the patient subcutaneously or intravenously in a controlled manner and at a predetermined flow rate.

Each dose 34 is selected and positioned initially in the container 12 as prescribed by the doctor so that, for example, the first does 34A is of low strength while the second 34B is of higher strength. With the knowledge of the dose's flow rate into the patient, as determined by the flow-resistance conduit 8, the duration of each dose fed to the patient can be easily predicted with certainty.

Considerable advantages accrue from this embodiment of the invention. For example, diabetics or other patients can be fed a preprogrammed insulin or other drug regime from a disposable low-cost drug-feeding device which requires no electrical motors or controllers; the capillary bore of the flow-resistance conduit 8 can be selected to give a known rate of feed which remains constant over a period of time; the drug doses 34 can be selected and positioned in the container 12 to give continuous or intermittent injection of the drugs, and flow can be easily interrupted manually at any time simply by kinking or applying pressure to the flexible tubing without damage to the apparatus.

Referring particularly to FIG. 4, the apparatus has at the free end of the resistance conduit 8 a male luer fitting 44 for fitment on the inlet end of the container 12 of FIG. 1 which has a complementary female fitting (not shown).

In FIG. 5, a saline reservoir 46 is located about one meter above the patient with a flexible tubing 48 leading the saline to the patient through an injection needle (not shown). A T-piece adaptor 50 is included in the tubing 48 and its branch leads through tubing 52 to a flow-resistance conduit 8 and balloon 2 similar to those shown in FIG. 4. The balloon 2 is filled with 100 ml of a drug to be injected into the patient without interruption of the saline flow from the reservoir 46. The pressure of the drug within the balloon 2 is equal to that of a two-meter column of water and the drug therefore is pressure-fed through the T-piece adaptor 50 into the tubing 48 and thence to the patient. Thus the drug is introduced without the requirement for nursing attention to switch the flow from saline to drug and back to saline.

The higher pressure in the balloon 2 than that provided by the reservoir 46 ensures that the balloon 2 does not reflate with saline after being emptied of drug. Thus the drug and saline supplies are connected in parallel rather than in series.

FIG. 6 shows how pressure of liquid in a balloon 2a can be maintained by connection with a further balloon 2b while feeding its liquid through a flow-resistance conduit 8a to a patient. The balloon 2b leads through a T-piece adaptor 4b and a further flow-resistance conduit 8b to an inflatable member 52 located within the balloon 2a. The flow-resistance conduits 8a and 8b are selected to allow the same rate of liquid flow through them, so that as fast as liquid flows from the balloon 2a its volume is replaced in balloon 2a by inflation of the member 52 by liquid from the balloon 2b.

The balloon 2b is larger and inflated to a greater pressure than the balloon 2a to ensure a positive flow to the balloon 2a. Thus the operating pressure of balloon 2b is 400 mm Hg (millimeters of mercury) while that of the balloon 2a is 200 mm Hg.

FIG. 7 illustrates the portable nature of an embodiment of the apparatus of the invention, with a main infusion line 54 terminating in a Y-piece adaptor 56 to which a balloon containing a drug is connected through a flow-resistance conduit 8. The balloon 2 empties itself over a period of 20 minutes and is replenished as required through a one-way valve 6.

FIGS. 8 and 9 show alternative embodiments of drug-feeding apparatus of the invention for providing both a supply of drugs and a flushing facility. In FIG. 8 the flushing is provided by a branch line 60 which by-passes the flow-resistance conduit 8, while in FIG. 9 the flushing is by way of a second balloon 2c downstream of the conduit 8 and isolated from it by a 3-way valve 62.

Figure 10:
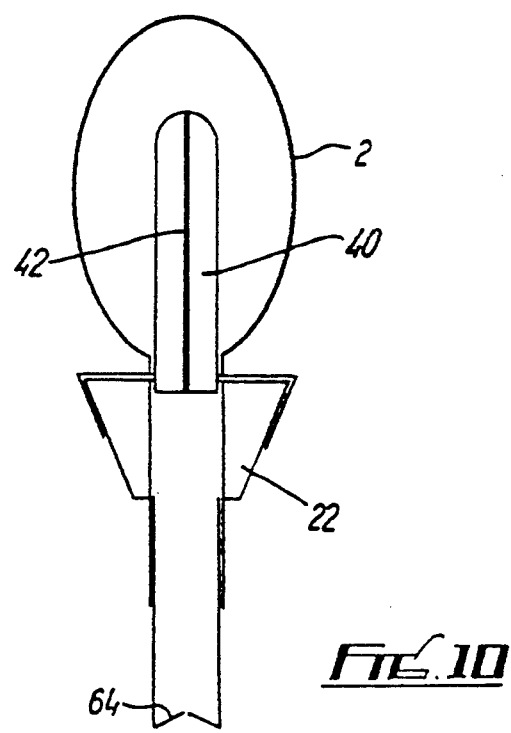
FIG. 10 shows a liquid storage system for use with apparatus of the invention.

The storage system of FIG. 10 terminates in a valve 64 and provides a pressurised inflated balloon 2 containing a drug for fitment to a flow-resistance conduit, thereby providing a rapid replacement for a depleted drug supply, or an alternative drug supply to one already being administered from a similar system, for example through an injection syringe.

The method can be applied for example to subcutaneous or intravascular injections.

Referring now to FIG. 11, a 20 cm length of flexible medical-grade polyvinyl chloride flow-resistance tubing 70 of 4 mm diameter has a through bore 72 of 0.068 mm diameter and terminates at one end in a male luer lock fitting 74 for connection to a feed tube and hypodermic needle. At its opposite, inlet end the tubing 70 is connected to a valve housing 76 having a one-way valve 78 and thence to a syringe 80 which is mounted on a fixed holder 82. The holder 82 is apertured at 84 to allow sliding passage of the body of the syringe 80 and a compression spring 86 bears against a shoulder 88 at the end of the body and against the portion of the holder 82 surrounding the aperture 84. The syringe has a piston 90 to which is fixed a piston rod 92 which fits within a recess 94 at a rear portion of the holder 82. The spring exerts a force equivalent to a head of 200 mm of mercury.

In use, the syringe is charged with a drug or other liquid through the one-way valve 78, causing the body of the syringe 80 to move to the right through the aperture 84 until it contains the desired amount of fluid. The spring 86 then causes the body to move to the left through the aperture, resulting in the piston 90 pressurising the fluid and forcing it through the bore 72 of the flow-resistance tubing 70. The length and diameter of the bore 72 dictate the rate of flow through it, and in this case the liquid passes at 0.2 ml per hour.

FIG. 12 shows an alternative arrangement for the syringe 80A. In this case the spring 86A is mounted within the body of the syringe to bear against the piston 90A. At its other end the spring 86a bears against a cap 96 fitted over the end of the syringe 80A. Thus the spring 86A pushes directly against the piston 90A to expel the liquid from the syringe 80A.

In FIG. 13 the reservoir is a flexible bag 100 disposed in a housing 102 between an end wall 104 and a movable plate in the form of a piston 106. The piston 106 is rotatably mounted on a screw-threaded rod 108 around which a pancake coil spring or "clock" spring 110 is located with the inner end of the spring 110 secured to the rod 108. The opposite end of the spring 110 is fixed to the housing 102.

The flexible bag 100 has an outlet 112 to which can be attached a flow line and flow restrictor as in the other embodiments.

In use of the FIG. 13 arrangement, the coil spring 110 is tensioned and as it unwinds it rotates the rod 108, causing the piston 106 to move towards the bag 100 and compress it against the wall 104 of the housing 102, thus ejecting its liquid contents through the outlet 112.

By selecting suitable pressures from the reservoir and suitable lengths and diameters for the bore through the flow-resistance capillary tubing, flow rates down to 0.1 millilitre per hour can be obtained with the methods and apparatus of the present invention.

By providing a flexible flow-resistance tube, the liquid flow rate can be controlled within fine tolerances and the length of the tube can be increased to reduce the flow rate. Such increases of the tube length does not interfere with the liquid feed, as the flexible tube not only performs the function of flow rate control but also provides at least a portion of the flexible feed tubing to the patient. Thus the tube does not render the apparatus unwieldy or obtrusive when substantial lengths are required, allowing much slower feed rates to be obtained than hitherto.

Figure 14:
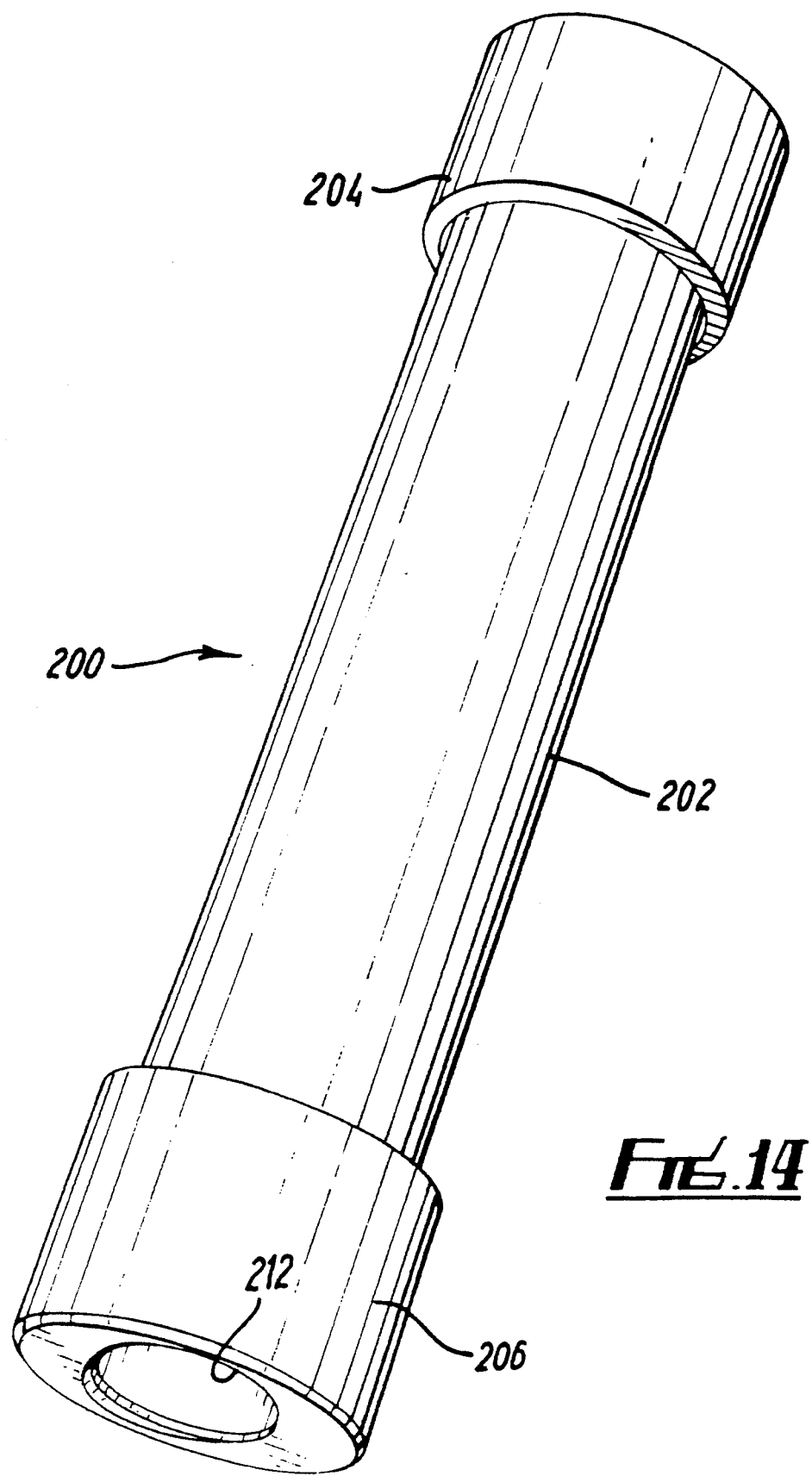
FIG. 14 is a perspective view of an embodiment of syringe driver in accordance with the present invention.

Referring now to FIG. 14; this shows a perspective view of a syringe driver 200 in accordance with the present invention. The syringe driver 200 comprises a hollow cylindrical body 202 closed at one end by fixed cap 204, and fitted at the other end with a bayonet coupling 206 by which the driver 200 is connectible to a syringe, as will be detailed below.

Figure 15:
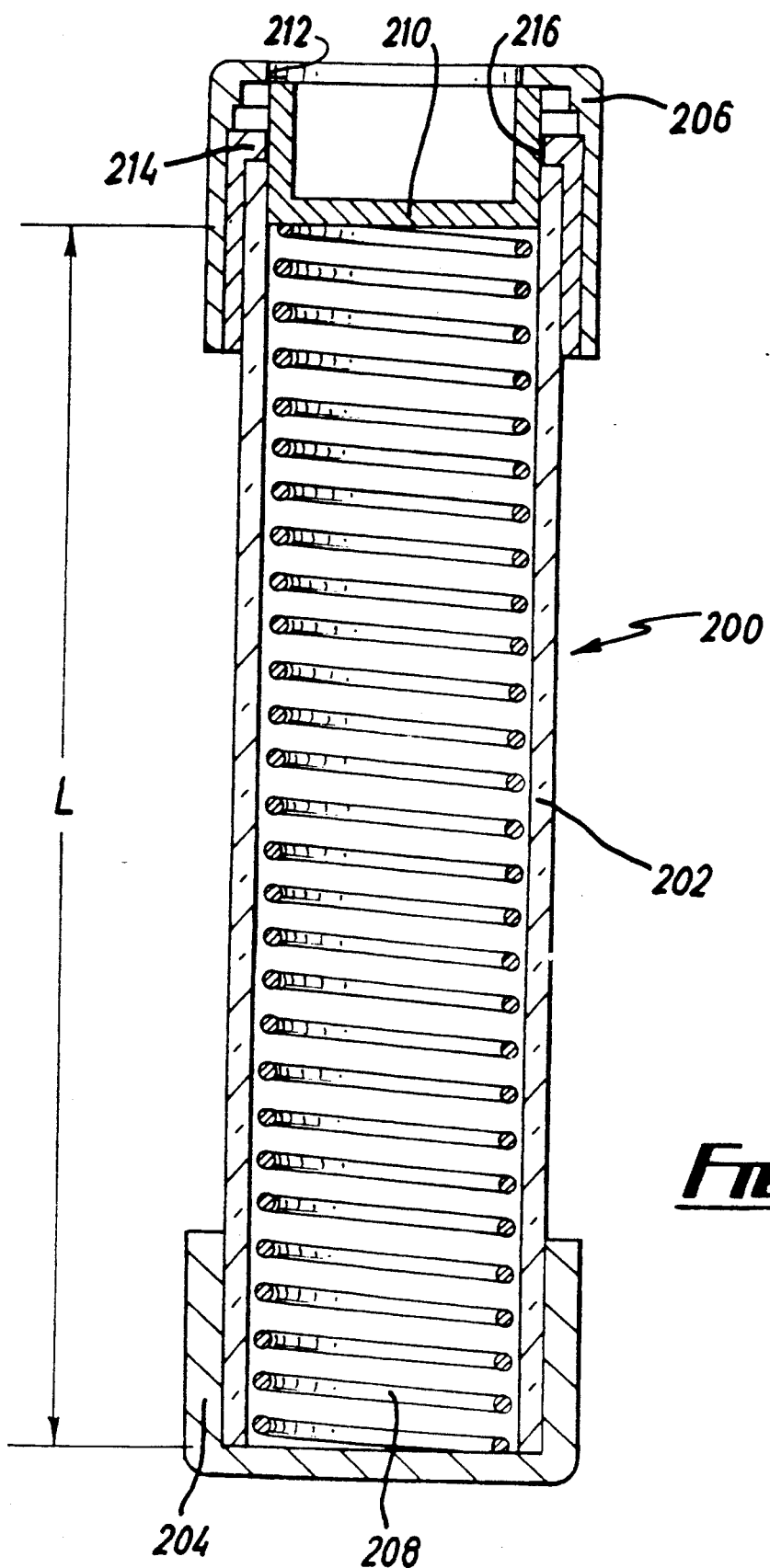
FIG. 15 is a longitudinal sectional elevation of the syringe driver of FIG. 14.

A longitudinal section of the syringe driver 200 of FIG. 14 is shown in FIG. 15, wherein it will be seen that the hollow cylindrical body 202 houses a helically-coiled compression spring 208, and a cup-shaped piston 210 which is slidable along the bore of the body 202. The spring 208 bears at one end against the piston 210 to drive the piston 210 along the bore of the body 202 towards the end of the body 202 fitted with the coupling 206, FIG. 15 showing the piston 210 having been fully displaced in this direction to its limit of movement as determined by its abutment with the coupling 206. The piston-driving expansion force of the compression spring 208 is reacted by abutment of the other end of the spring 208 against the interior of the fixed end closure cap 204.

The housing-defined maximum length to the spring 208 within the spring-housing body 202, i.e. with the piston 210 abutting the coupling 206 as shown in FIG. 15, is the length "L" between the inside of the end cap 204 and the inside face of the piston 210.

The spring 208 is formed to have a free length "A" i.e. the length of the spring 208 between its opposite ends when allowed to expand to its natural unconstrained length when free of the syringe driver 200 or of any other constraint.

Conversely, the spring 208 has a yield-point length "S", i.e. the length when the metal of the spring 208 is compressed to the extent of its elastic modulus and loses its resilience, corresponding to the maximum compressive force that can be applied to the spring 208 without exceeding its elastic limit and hence still exhibiting a substantially linear force/displacement characteristic.

The syringe driver 200 provides a syringe-driving force output (in a manner detailed subsequently) which varies by less than a predetermined limit over the full travel of the syringe plunger, by selection of the above-defined dimensions to have a predetermined interrelationship as will now be detailed.

The peak syringe-driving spring force required to be delivered determines the particular spring to be selected, on the basis of this force being the compressive force required to compress the selected spring to its length "S".

Given a particular syringe driver 200 having a characteristic internal dimension "L" as previously defined, and the requirement to deliver a minimum syringe-driving spring force diminished by not more than a proportion "R" from the aforementioned peak force, this then gives the spring selection formula:

"L not less than [R (A−S)+S]"

In the particular case where the minimum syringe-driving spring force is to be greater than two-thirds of the peak syringe-driving spring force, this gives a spring selection formula: "A greater than (3L−2S)".

In another particular case where the syringe-driving spring force is allowed a variation of less than plus or minus ten per cent (i.e. a spring force diminution "R" from peak of less than twenty per cent), this gives a spring selection formula: "A greater than (5 L−4S)".

Figure 18:
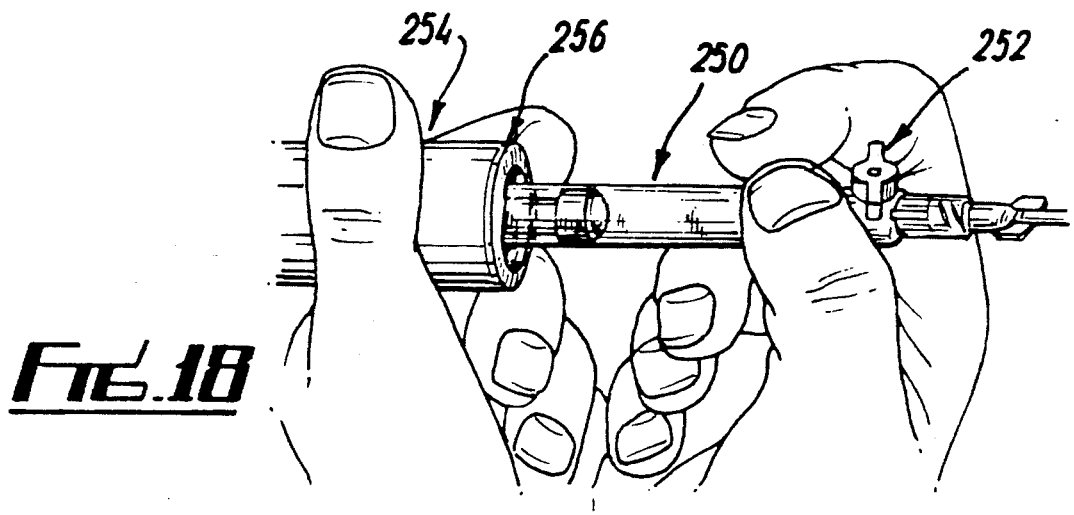

Turning now to details of the bayoner coupling 206, this is shaped and dimensioned to connect to the two laterally-extending finger grips (see FIG. 16) of a standard syringe barrel by which the barrel can be digitally restrained while simultaneously depressing To this end, the coupling 206 presents an ovoidal hole 212 (see particularly FIG. 14) into which the finger grips can be inserted by longitudinally inserting the plunger end of the syringe into the syringe driver 200 (See FIG. 18). Over-insertion of the finger grips is prevented by providing an inner member of the coupling 206 in the form of a collar 214 fitted over the end of the syringe driver body 202 and under the coupling 206. The collar 214 has a circular end opening 216 of a diameter just sufficient to pass the skirt of the piston 210 but insufficient to pass the syringe finger grips therethrough. (The lesser width of the ovoidal coupling hole 212 prevents outward passage of the circular rim of the skirt of the piston 210 while being just sufficient to admit the end of the syringe barrel between the finger grips). When the syringe is so inserted (as shown in FIG. 18), the outer end of the syringe plunger will have forced the piston 210 down the bore of the driver body 202, at least partially compressing the spring 208 which in turn outwardly biasses the syringe as a whole. The syringe barrel is then manually twisted, relative to the syringe driver 200, by one-quarter turn to bring the diametrically-opposed finger grips under the overhanging edges across the lesser width of the ovoidal coupling hole 212 whereupon manual insertion force on the syringe barrel is released to allow the outward bias of the spring 208 to latch the finger grips into stably retained positions inside these overhanging edges.

The bayonet coupling 206 thus allows easy and rapid connection of the syringe driver 200 to a standard syringe, without the need of tools. Moreover, by selecting a spring 208 in accordance with the above-described spring selection formula, the syringe-driving spring force will vary throughout the full travel of the syringe plunger by less than a predetermined limit.

Figure 16:
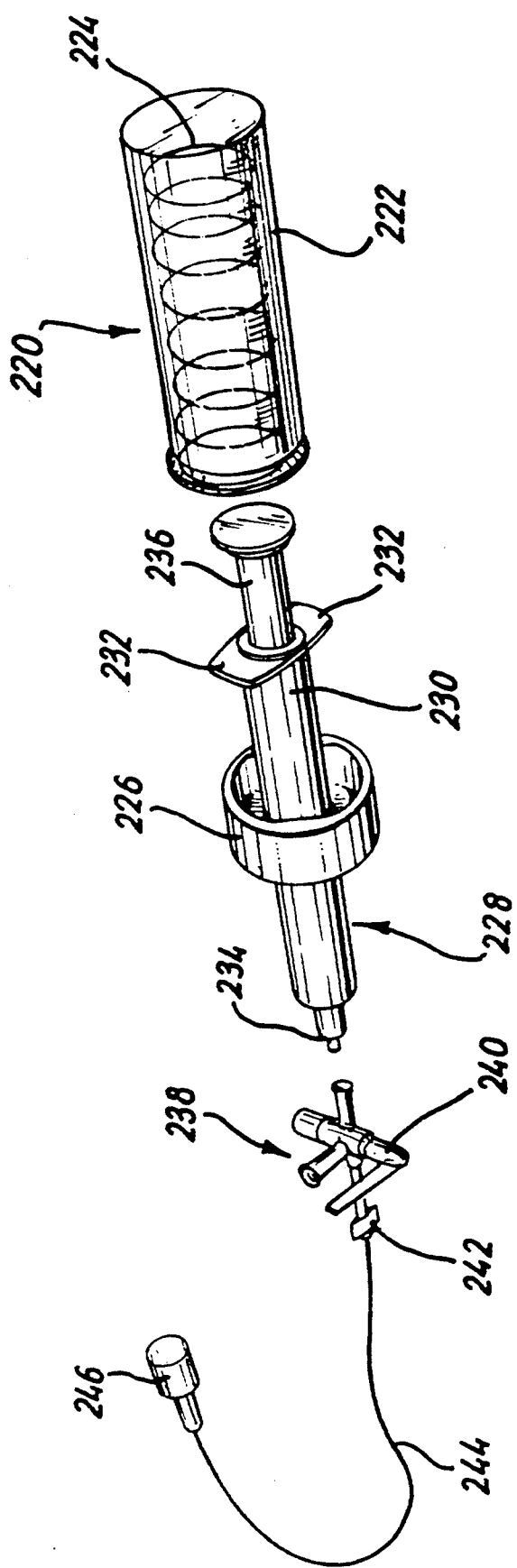
FIG. 16 is an exploded perspective view of another embodiment of syringe driver, in association with a syringe, a length of capillary tubing, a tap, and a cannula.

FIG. 16 shows a similar but modified embodiment of syringe driver 220 comprising a hollow tubular body 222 closed at one end and housing a syringe-driving spring 224 selected in accordance with the spring selection formula described above with reference to FIGS. 14 and 15. Normally attached to the other end of the body 222 (but shown separately in the exploded perspective assembly view of FIG. 16) is a syringe coupling 226 in the form of a detachable collar.

The syringe driver 220 is shown in pre-assembly configuration with a syringe 228 comprising a cylindrical syringe barrel 230 having an opposed pair of projecting finger grips 232 at one end and a barrel bore liquid outlet 234 at the other end. A syringe plunger 236 (of which only the outer end is visible in FIG. 16) is slidably sealed to the bore of the syringe barrel 230 to displace liquid in the syringe barrel 230 out of the outlet 234 as the syringe plunger 236 is pressed down the bore of the syringe barrel 230.

To assemble the drug-feeding apparatus illustrated in FIG. 16, the syringe 228 is filled with a liquid drug or other injectable liquid, and the coupling collar 226 is loosely placed around the syringe barrel 230. Next, the syringe outlet 234 is controllably blocked by attachment of a tap 238 (shown by way of example as a change-over valve controlled by an integral manually-operated control member 240). With the tap 238 temporarily closed to block outflow of liquid from the syringe outlet 234, the syringe driver 220 is forced down onto the outer end of the syringe plunger 236, compressing the spring 224 to less than its housing-defined length (shown as the length "L" in the equivalent arrangement of FIG. 15). The coupling collar 226 is then moved up the syringe barrel 230 to trap the finger grip projections 232 against the open end of the syringe driver body 222, and there secure them by fastening the collar 226 to the body 222, e.g. by means of mutually co-operating screw threads or by a bayonet connector.

The outlet 242 of the tap 238 passes by way of a length of flow-restricting flexible thick-wall capillary tubing 244 to a downstream-end fitting 246 (shown in the form of a female luer lock fitting) for attachment to a cannula (not shown) or other device for injection of the syringe-contained liquid into the patient. The length and bore of the tubing 244 are selected to control the rate of liquid feed to the patient to a desired low flow rate.

Figure 17:
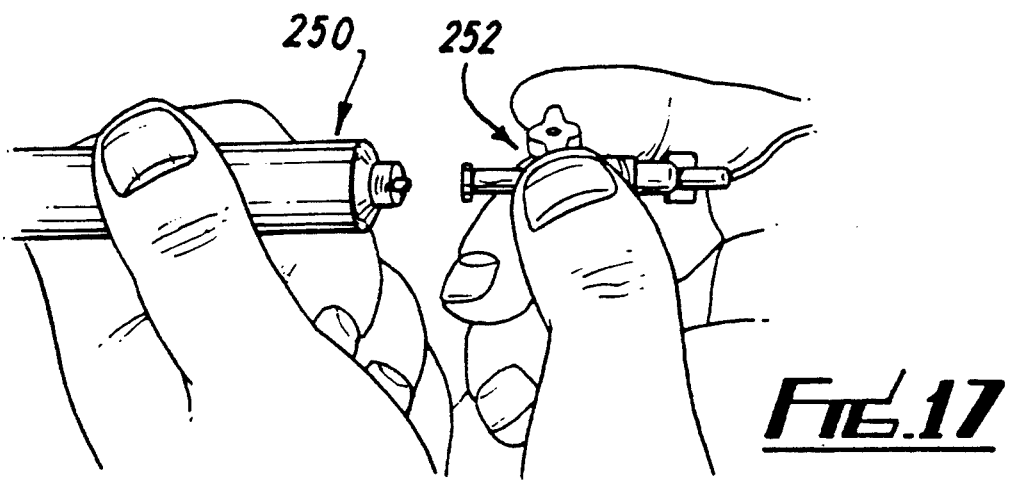
FIGS. 17, 18 and 19 show three successive stages in the assembly and installation of a patient-borne drug-feeding system in accordance with the present invention.
Figure 19:
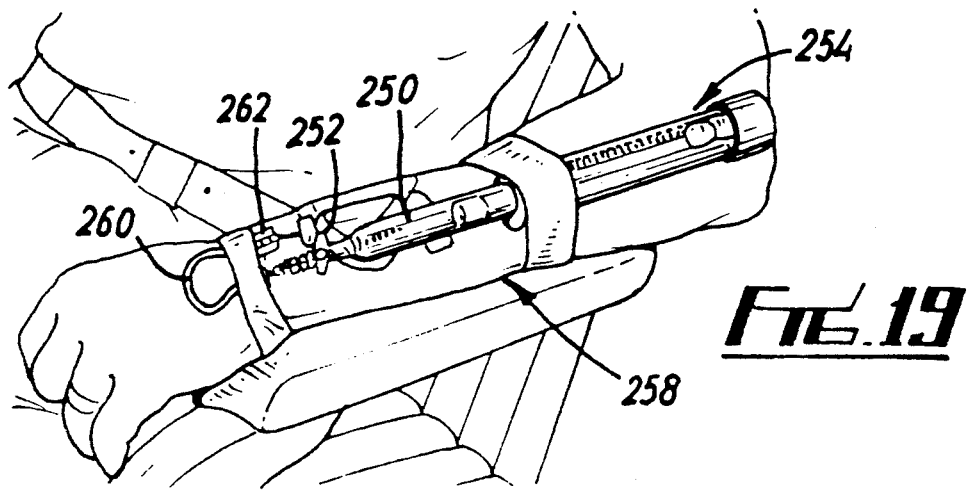

The sequence of assembly and attachment to a patient of a generally similar drug-feeding apparatus is depicted in FIGS. 17, 18 and 19.

FIG. 17 shows a liquid-filled syringe 250 having a temporarily-closed outlet control tap 252 being manually attached thereto.

FIG. 18 shows the pre-loaded and outlet-controlled syringe 250 being manually attached to a spring-powered syringe driver 254 of the type shown in FIGS. 14 and 15 by means of a bayonet coupling 256 as described with reference thereto.

FIG. 19 shows the syringe 250 and the coupled syringe driver 254 mounted on the forearm 258 of a drug-recipient patient to have the drug controllably transferred to the patient (when the tap 252 is opened) at a flow rate controlled by the pre-selected length and bore diameter of the length of flow-restricting flexible thick-wall capillary tubing 260 acting as a liquid conduit through which the liquid is transferred from the syringe 250 through the downstream-end cannula 262 and into the patient.

FIG. 19 particularly illustrates how the present invention provides a compact and gravity-independent drug feed to the patient while allowing the patient substantial freedom of mobility, and without requiring the relatively complex and expensive electric-motor-driven and microprocessor-controlled infusion systems of the prior art.

While certain modifications and variations of the invention have been described above, the invention is not restricted thereto, and other modifications and variations of the invention can be adopted without departing from the scope of the invention as defined in the appended claims.

I claim:

1. Liquid-feeding apparatus for feeding a liquid to a recipient at a rate of less than 1 millilitre per hour, said apparatus comprising:
   (a) a pressurisable source of the liquid;
   (b) said source having a liquid outlet;
   (c) a transfer fitting for transfer of the liquid to the recipient;
   (d) a liquid conduit coupling said liquid outlet of said source to said transfer fitting for conveying the liquid from said source to said transfer fitting;
   (e) said liquid conduit comprising a liquid flow restriction;
   (f) said liquid flow restriction comprising a length of flexible thick-wall capillary tubing;
   (g) said tubing having a ratio of the external diameter thereof to the bore diameter thereof in excess of 2:1;
   (h) said tubing having a bore diameter of less than about 250 microns; and
   (i) said tubing having a length of less than about 40 centimeters.

2. Apparatus as claimed in claim 1, wherein said tubing has a length of about 8 centimeters.

3. Apparatus as claimed in claim 1, wherein said pressurisable source comprises a container having a variable internal volume and pressurisation means stressing said container to tend to reduce the internal volume thereof.

4. Apparatus as claimed in claim 3 wherein said container and said pressurisation means are conjoined as an elastically expandible bladder.

5. Apparatus as claimed in claim 4, wherein said bladder contains an insert having a volume greater than the internal volume of said bladder in the unexpanded state thereof.

6. Apparatus as claimed in claim 3, wherein said container comprises a syringe having a body with a bore therein and a plunger slidingly sealed to said bore to define said variable internal volume, and wherein said pressurisation means comprises a housing and an elastically compressible spring therein, said housing having a coupling by which said housing is connectible to said body of said syringe, said spring being disposed within said housing to have one end of said spring act on said plunger of said syringe when said housing is connected to said body of said syringe to have the other end of said spring react against said housing, said spring being dimensioned and precompressed to act on said plunger with a force that varies over the full travel of said plunger by less than a predetermined limit.

7. Apparatus as claimed in claim 6, wherein said body of said syringe comprises an opposed pair of projections functioning as finger grips in manual operation of said syringe, and wherein said coupling is a bayonet coupling dimensioned to connect to said projections.

8. Apparatus as claimed in claim 6, wherein said spring is a helically-coiled compression spring having a free length equal to A, a yield-point length equal to S, and a housing-defined maximum length within the housing equal to L, and wherein the spring and the housing are so dimensioned that A is greater than or equal to $3L-2S$.

9. Apparatus as claimed in claim 8, wherein the spring and the housing are so dimensioned that A is greater than or equal to $5L-4S$.

10. Syringe-driver apparatus for driving a syringe, the syringe comprising:
    (a) a syringe body having bore therein and a liquid outlet at one end of said bore, and an opposed pair of projections functioning as finger grips in manual operation of the syringe; and
    (b) a syringe plunger slidable within said bore and forming a seal therewith to define a variable volume within said bore between said plunger and said liquid outlet, said volume being varied by travel of said plunger along said bore;
said syringe-driver apparatus comprising a housing and a spring means including an elastically compressible spring therein, said housing having a bayonet coupling dimensioned to connect to said projections, and by which said housing is connectible to said syringe body, said spring being disposed within said housing to have a first end of said spring urge said syringe plunger when said housing is connected to said syringe body and to have a second end of said spring react against said housing, said spring means for urging said syringe plunger with a force that varies over the full travel of said syringe plunger by less than a predetermined limit.

11. Syringe-driver apparatus as claimed in claim 10, wherein said spring is a helically-coiled compression spring having a free length equal to A, a yield-point length equal to S, and a housing-defined maximum length within said housing equal to L, and wherein said spring and said housing are so dimensioned that A is greater than or equal to $3L-2S$.

12. Syringe-driver apparatus as claimed in claim 11, wherein said spring and said housing are so dimensioned that A is greater than or equal to $5L-4S$.

* * * * *